(12) United States Patent
Johnson et al.

(10) Patent No.: US 9,814,899 B2
(45) Date of Patent: Nov. 14, 2017

(54) SYSTEMS AND METHODS FOR IN VIVO IRRADIATION OF BLOOD

(71) Applicant: UVL Blood Labs, Inc., Santa Barbara, CA (US)

(72) Inventors: Scot Johnson, Lutz, FL (US); Michael Harter, Tampa, FL (US)

(73) Assignee: UVLrx Therapeutics, Inc., Santa Barbara, CA (US)

( * ) Notice: Subject to any disclaimer, the term of this patent is extended or adjusted under 35 U.S.C. 154(b) by 143 days.

(21) Appl. No.: 14/323,244

(22) Filed: Jul. 3, 2014

(65) Prior Publication Data

US 2015/0018753 A1 Jan. 15, 2015

Related U.S. Application Data

(60) Provisional application No. 61/957,463, filed on Jul. 3, 2013, provisional application No. 61/957,513, filed
(Continued)

(51) Int. Cl.
*A61N 5/06* (2006.01)
*A61B 17/00* (2006.01)
*A61B 90/98* (2016.01)

(52) U.S. Cl.
CPC ......... *A61N 5/0601* (2013.01); *A61N 5/0624* (2013.01); *A61B 90/98* (2016.02); *A61B 2017/00176* (2013.01); *A61N 2005/0602* (2013.01); *A61N 2005/063* (2013.01); *A61N 2005/0626* (2013.01); *A61N 2005/0661* (2013.01); *A61N 2005/0662* (2013.01)

(58) Field of Classification Search
CPC .... A61N 5/062; A61N 5/0624; A61N 5/0601; A61N 2005/0661; A61N 2005/0662; A61N 2005/0626; A61B 90/98; A61B 2017/00176; A61B 2005/0602; A61B 2005/0626; A61B 2005/063; A61B 2005/0661; A61B 2005/0662
USPC .............................. 607/88, 94, 92
See application file for complete search history.

(56) References Cited

U.S. PATENT DOCUMENTS

| 4,693,556 A | 9/1987 | McCaughan, Jr. |
| 5,505,725 A | 4/1996 | Samson |

(Continued)

FOREIGN PATENT DOCUMENTS

| EP | 0951305 B1 | 10/2004 |
| EP | 2179767 A1 | 4/2010 |
| WO | 2006128047 A2 | 11/2006 |

*Primary Examiner* — Michael Carey
(74) *Attorney, Agent, or Firm* — Fish IP Law LLP

(57) ABSTRACT

Systems and methods for illumination of a vascular space and its contents using an electromagnetic energy source that supplies a plurality of wavelengths ranging from ultraviolet to infrared are shown. Illumination can be performed using multiple wavelengths, simultaneously or sequentially, and can be performed in accordance with a protocol where an initial illumination produces an effect that is at least partially reversed by a subsequent illumination. Illumination protocols can be stored on a database and accessed via a user interface displayed on the electromagnetic energy source. The database can be used to store data related to performance of system components, and such data can be used to override or modify an illumination protocol.

14 Claims, 9 Drawing Sheets

Related U.S. Application Data on Jul. 5, 2013, provisional application No. 61/887,845, filed on Oct. 7, 2013, provisional application No. 61/887,800, filed on Oct. 7, 2013.

(56) References Cited

U.S. PATENT DOCUMENTS

| | | |
|---|---|---|
| 6,312,593 B1 | 11/2001 | Petrie |
| 6,908,460 B2 | 6/2005 | DiStefano |
| 8,460,229 B2 | 6/2013 | Dacey, Jr. et al. |
| 2003/0097122 A1* | 5/2003 | Ganz ............... A61B 18/18 606/7 |
| 2003/0114842 A1* | 6/2003 | DiStefano ......... A61B 18/24 606/7 |
| 2003/0127603 A1 | 7/2003 | Horowitz et al. |
| 2004/0073278 A1 | 4/2004 | Pachys |
| 2004/0186407 A1 | 9/2004 | Walker et al. |
| 2005/0159794 A1 | 6/2005 | Neuberger |
| 2005/0177208 A1* | 8/2005 | Irwin ............... A61N 5/0603 607/94 |
| 2006/0036164 A1* | 2/2006 | Wilson .............. A61B 5/06 600/424 |
| 2011/0152752 A1* | 6/2011 | Dacey, Jr. ......... A61L 2/0011 604/21 |
| 2013/0101464 A1 | 4/2013 | Smyczynski |

* cited by examiner

| Virus | Reported effective UV fluence (mJ/cm2) | | Bacteria | Reported effective UV fluence (mJ/cm2) |
|---|---|---|---|---|
| Poliovirus type 1 | 5-50 | | Salmonella typhi | 2-10 |
| Adenovirus ST2, 15, 40, 41 | 8-306 | | Campylobacter jejuni | 0.5-6 |
| Adenovirus ST40 | 8-184 | | Yersenia enetercolitica | 0.6-5 |
| Adenovirus ST2, 41 | 30-90 | | Shigella dysenteriae | 1-5 |
| Rotavirus SA-11 | 5-50 | | Shigella sonnei | 3-8 |
| Calicivirus feline, canine | 4-49 | | Vibrio cholerae | 0.6-4 |
| Calicivirus bovine | 2-33 | | Legionella pneumophila | 0.5-12 |
| Hepatitis A | 5-28 | | Escherichia coli | 1-15 |
| Coxsackie virus B5 | 5-40 | | Streptococcus faecalis | 2.5-16 |
| MS2-phages | 5-139 | | Bacillus subtilis | 5-78 |
| Phi X174 | 2-12 | | Clostridium perfringens | 48-64 |
| PRD1 | 9-35 | | | |
| B40-8 | 1-39 | | Eukaryote | Reported effective UV fluence (mJ/cm2) |
| T7 | 5-20 | | Cryptosporidium parvum | 2-10 |
| Q Beta | 10-50 | | Campylobacter jejuni | 0.5-6 |
| | | | Yersenia enetercolitica | 0.6-5 |
| | | | Shigella dysenteriae | 1-5 |

Figure 7

SYSTEMS AND METHODS FOR IN VIVO IRRADIATION OF BLOOD

This application claims priority to U.S. Provisional Application No. 61/957,463 filed on Jul. 3, 2013, U.S. Provisional Application No. 61/957,513 filed on Jul. 5, 2013, U.S. Provisional Application No. 61/887,845 filed on Oct. 7, 2013, and U.S. Provisional Application No. 61/887,800 filed on Oct. 7, 2013. These and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

This application is related to co-pending U.S. patent application Ser. No. 14/323,217, titled "Vascular Access Device with Integrated Light Guide", co-pending international patent application number PCT/US14/45460, titled "Vascular Access Device with Integrated Light Guide", co-pending U.S. patent application Ser. No. 14/323,180, titled "Sheathed Optical Fiber", and co-pending international patent application number PCT/US14/45449, titled "Sheathed Optical Fiber". All of these co-pending U.S. and international patent applications are incorporated by reference herein in their entirety.

FIELD OF THE INVENTION

The present invention generally relates to devices and methods for illumination or irradiation of blood. More particularly, the present invention relates to devices and methods for irradiating human blood in vivo.

BACKGROUND

The following description includes information that may be useful in understanding the present invention. It is not an admission that any of the information provided herein is prior art or relevant to the presently claimed invention, or that any publication specifically or implicitly referenced is prior art.

It has long been accepted that certain wavelengths of electromagnetic radiation, such as ultraviolet light, have the ability to affect biological and chemical structures. For example, the formation of thymine dimers under the influence of ultraviolet light is well known and has been utilized to sterilize surfaces by killing or inactivating a variety of pathogens. In the early 1900's efforts were made to incorporate exposure to ultraviolet light as a treatment modality for various diseases, including bacterial and viral infections. Procedures were typically extracorporeal; a volume of blood would be removed from a patient, irradiated to modify a patient's immune response and/or decrease the bacterial or viral load, and returned to the patient. Such efforts were hindered, however, by the sources of ultraviolet light available at the time. UV lamps of the time period did not operate reliably, produced inconsistent illumination, and generated large amounts of heat. The development of effective and reliable antibiotics that were easily administered resulted in a loss of interest in this therapeutic approach.

The increasing prevalence of antibiotic-resistant pathogens and the recognition of potential effectiveness for the treatment of noninfectious medical conditions has led to an increasing interest in the use of blood irradiation as a treatment modality. A variety of devices for improved extracorporeal irradiation of blood have been proposed. For example, International Patent Application Publication No. WO2006/128047 (to Petrie) and United States Patent Application Publication No. 2006/0157426 (to Petrie) disclose devices for the irradiation of volumes of blood taken from a patient using devices that expose blood ultraviolet light, and incorporate shutters that allow control of the degree of irradiation. Other extracorporeal devices have included mechanisms for mixing the volume of blood taken from the patient in order to improve exposure during the irradiation process. Both active agitation of blood (European Patent No. EP0951305B1, to Morris) and use of static mixers with plasma preparations (United States Patent Application Publication No. 2003/127,603, to Horowitz et al) have been disclosed. Approaches involving the removal and reinfusion of a specific volume of blood are, however, necessarily limited in their ability to irradiate large blood volumes from an individual. In addition, they expose the patient to the risk of reinfusion with treated blood from a different individual, through either mislabeling or human error. The extensive exposure of blood to non-biological surfaces also carries with it the risk of unwanted clotting and resulting embolisms. While this is, to some extent, preventable through the use of anticoagulants the use of such substances also carries substantial risk.

Approaches in which blood is removed, irradiated, and returned to the patient in a continuous fashion have been described (United States Patent Application Publication No. 2013/0101464 to Smyczynski). Similarly, United States Patent Application Publication No. 2004/0186407 (to Walker) teaches a semi-batch approach, in which from a patient is collected in a reservoir, irradiated with ultraviolet light while contained as a thin film, and then returned to the patient in a cyclical fashion. Such extracorporeal approaches, however, still necessarily involve the use of complex equipment, damage to blood cells and platelets through exposure to equipment surfaces, and formation of blood clots.

Alternative methods for the irradiation of blood have been proposed. For example, European Patent Application No. 2,179,767 A1, to Kokos and Jurinyi, discloses a device for irradiation of blood through the membranes of the patient's nasal mucosa. Various devices have also been developed that permit direct irradiation of blood or tissue within the vasculature or body cavity of a patient. For example, U.S. Pat. No. 4,693,556 (to McCaughan) describes placing an optical fiber equipped with an optical radiator into a body cavity. The use of multiple waveguides providing ultraviolet light to an implanted catheter for the purpose of reducing catheter-associated infections in described in U.S. Pat. No. 8,460,229 (to Dacey). It is not clear, however, how effective approaches are in irradiating blood.

Attempts have also been made to irradiate blood while it is within the vascular system. U.S. Pat. No. 5,505,725 (to Samson) and U.S. Pat. No. 6,908,460 (to DiStefano) describe devices that place a conventional optical fiber directly in a vein by inserting it through a hypodermic needle following venipuncture. Such approaches, however, fail to provide for the accidental breakage of the inserted optical fiber and the subsequent loss of efficient irradiation and release of the resulting fragments into circulation. Such breakage is a known issue with quartz or silica materials that are typically utilized in optical fibers, particularly when subjected to relatively sharp bends such as upon insertion into a vein. In addition, such optical fibers lack sufficient rigidity to remain in one position within a vein when subjected to the pulsatile flow of blood, and may collide with and damage the interior of the vein.

While ultraviolet light, which has a known germicidal effect, has been used by a number of investigators for irradiation of blood (as noted above), other wavelengths of light have also been considered. For example, United States Patent Application Publication No. 2004/0073278 (to Pachys) describes an implanted light sources for irradiation of body tissues that has selectable frequencies. U.S. Pat. No. 6,908,460 (to DiStefano) discusses alternating between ultraviolet and visible wavelengths during irradiation. Other investigators have suggested combining different wavelengths during irradiation, as discussed in U.S. Pat. No. 8,460,229 (to Dacey et al). The rationale for changing or combining frequencies of light during irradiation, however, is not clear in these.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

While certain devices and methods are known in the art to irradiate blood, all or almost all of them suffer from one or more disadvantages. Thus, there is still a need for simple device for the effective in vivo irradiation of blood.

SUMMARY OF THE INVENTION

The inventive subject matter provides systems and methods that provide for safe and efficient illumination of vascular spaces and their contents. Disclosed systems provide a source of electromagnetic energy that is coupled to one or more devices that access the vascular system and introduce a waveguide. Such systems can provide different wavelengths or wavelength ranges, and can supply one or more of such wavelength(s) or wavelength range(s) to a single waveguide simultaneously. In methods of the inventive concept the waveguide provides illumination for a prescribed period of time, and can provide multiple periods of illumination wherein each period provides illumination with a different wavelength/wavelength range or set of wavelengths/wavelength ranges. The different wavelengths or wavelength ranges can be selected to have different effects, such as inducing damage to select cells or molecules or repairing or inducing repair of such damage. Such systems and methods can be used for irradiation of blood in vivo.

One embodiment of the inventive concept is a method for intravenous irradiation of blood in which a vascular access device is used to place at least part of a waveguide within a vascular space. A first illumination (for example, with ultraviolet light such as UV-B or UV-C or a combination of ultraviolet light such as UV-B or UV-C and light ranging from 620 nm to 640 nm) is transmitted to the vascular space and its contents via the waveguide for a period of time to induce a first effect, then a second illumination (for example, light ranging from 520 nm to 540 nm or a combination of light ranging from 520 nm to 540 nm and light ranging from 620 nm to 640 nm) is transmitted via the waveguide for a period of time that reverses, at least partially, the effect of the first illumination. These time intervals can be 1 second or longer. In such an embodiment of the inventive concept, a fluid can be delivered to the vascular space through the vascular access device during illumination.

Another embodiment of the inventive concept is a source of electromagnetic energy for illumination of a vascular space. Such a source of electromagnetic energy can include two or more emitters of electromagnetic energy (for example, light emitting diodes), at least one optical cable connector that is in optical communication with one or more of the emitters of electromagnetic energy, and at least one optical cable that includes a hub which provides an optical interface with the optical connector. The hub can include mechanisms that obtain and transmit identification data unique to an optical cable to the processor and/or the database. The electromagnetic energy source also includes a processor that can modulate the optical communication between the electromagnetic energy emitters and the optical cable connector (for example, using an optical switch and/or optical router), and a database that is communicatively linked to the processor. The database is used for storage of illumination protocols, which include instructions for the modulation of an electromagnetic energy emitter. The electromagnetic energy also has a calibration port, which provides data related to performance of system components (for example, an electromagnetic energy emitters, optical cable connector, optical cable, or vascular access device) to the database. In some embodiments of the inventive concept the processor is configured to generate modified illumination protocol from a base illumination protocol based on such data. The electromagnetic energy source can also include a mount that permits a user to secure the electromagnetic energy source, for example to an IV pole.

In some embodiments the electromagnetic energy source includes at least two optical cable connectors and at least two optical cables. In such embodiments the electromagnetic energy source can supply electromagnetic energy from a single electromagnetic energy emitter to both optical cables simultaneously. In other embodiments the electromagnetic energy source can supply electromagnetic energy from two different electromagnetic energy emitters to the same optical cable, either sequentially or simultaneously.

Another embodiment of the inventive concept is a system for illumination of a vascular space that includes an electromagnetic energy source with two or more electromagnetic energy emitters, a vascular access device that includes a waveguide, an optical cable that provides optical communication between the electromagnetic energy emitter and the waveguide, and a calibration port. The calibration port can be placed in optical communication with an electromagnetic energy emitter, for example via an optical cable. The system includes a processor that can modulate the optical connection between at least one of the electromagnetic energy emitters and the optical cable, and which is in communication with a database that includes instructions for doing so. In some embodiments the system includes two or more optical cables and two or more vascular access devices. The system can include an optical calibrator, which can be optically coupled to an electromagnetic energy emitter. In some embodiments of the inventive concept the vascular access device includes a catheter; at least part of the waveguide lies within a lumen of the catheter, such that the entire waveguide is enclosed within such a vascular access device.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1A provides a diagrammatic view of an electromagnetic energy source of the inventive concept. FIG. 1B provides a representative view of an electromagnetic energy source of the inventive concept.

FIG. 7 shows varying susceptibility of different pathogens to ultraviolet radiation.

DETAILED DESCRIPTION

Figure 1A:
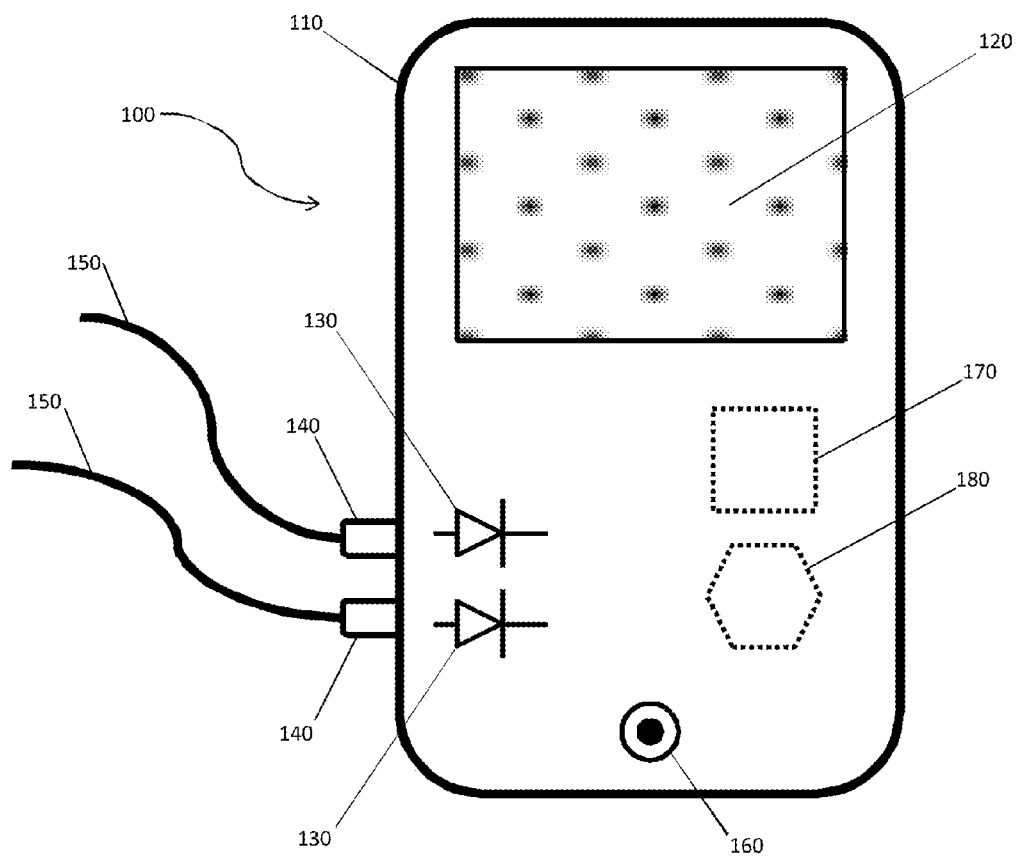
FIG. 1A and FIG. 1B represent electromagnetic energy sources of the inventive concept.

The inventive subject matter includes methods and systems that can be used for illumination and/or irradiation of intravascular spaces (for example, the interior of a peripheral vein) and their contents. Systems of the inventive concept can a source of electromagnetic energy (for example, ultraviolet, visible, and/or infrared light) that includes a housing, one or more sources of electromagnetic radiation (for example, a light emitting diode), and can optionally include one or more waveguides configured to interface with the source of electromagnetic energy and to transmit the electromagnetic energy to a device configured to provide access to an intravascular space. Such a system can include features for verifying physical attachment and/or optical communication between a source of electromagnetic energy and a waveguide, and can include one or more features that permit the identification of individual waveguides. Systems of the inventive concept can also include a vascular access device (VAD) that includes a cannula or catheter suitable for intravenous placement, a waveguide (at least a portion of which lies within the cannula or catheter), and a coupling that places the waveguide in optical communication with an optical cable. Such a cannula or catheter can be suitable for use in the peripheral vasculature, the central vasculature, or both. Methods of the inventive concept include provision of a VAD and placement of a waveguide-containing portion of the VAD within an intravascular space. The waveguide is placed in optical communication with a source of electromagnetic energy, and can transmit such electromagnetic radiation to the intravascular space and its contents in the form of a first irradiation to fluids and/or cells within a vascular space (i.e., a vein, artery, and/or lymphatic channel), followed by the transmission of a second irradiation in which therapeutic light of a different wavelength or wavelength range is applied. In some embodiments the first irradiation can result in changes to cellular and/or molecular structures of fluids and/or cells that are at least partially reversed by the second irradiation (typically only in non-pathogenic cells or tissue). For example, the second illumination can provide one or more suitable wavelengths at an intensity and/or period of time that promotes the activity of reparative enzymatic and non-enzymatic pathways in a vertebrate, thereby at least partially repairing the effects of the first illumination. In some embodiments of the inventive concept an irradiation can be polychromatic (i.e. composed of electromagnetic radiation that includes more than one set of wavelength ranges).

Various objects, features, aspects and advantages of the inventive subject matter will become more apparent from the following detailed description of preferred embodiments, along with the accompanying drawing figures in which like numerals represent like components. The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

Systems of the inventive concept include a source of electromagnetic energy, a device for providing optical access to a vascular space, and device for conducting or otherwise directing electromagnetic energy (for example, an optical cable) that serves to provide an optical connection between the source of electromagnetic energy and the optical access to the vascular space. The source of electromagnetic energy can include one or more emitters of electromagnetic radiation. Such an emitter can be selected to produce electromagnetic energy in the form of ultraviolet (for example UVA, UVB, and/or UVC), visible, and/or infrared light. Such light can be coherent or incoherent. Examples of suitable emitters include incandescent lights, metal vapor lamps, HID lamps, fluorescent lamps, lasers, gas lasers, LED lasers, light emitting diodes, or combinations of these. When polychromatic emitters are used, the source of electromagnetic energy can include a device that permits selection of desired wavelengths and/or wavelength ranges. Examples of such devices include prisms, wide bandwidth filters, narrow bandwidth filters, polychromatic filters, diffraction gratings, and combinations thereof. Alternatively, monochromatic emitters can be used.

A source of electromagnetic energy can be configured to provide a plurality of different wavelengths or wavelength ranges, sequentially and/or simultaneously. Towards that end a source of electromagnetic energy and can also include devices for distribution of electromagnetic energy (for example, an optical router, an optical switch, optical fibers, and associated connectors). In such an embodiment, the source of electromagnetic energy can couple a plurality of emitters to an optical cable, such that a plurality of wavelengths or wavelength ranges can be provided to a single optical cable. For example, a source of electromagnetic energy can include a set of emitters, an optical router, and an interface for an optical cable. In use, such a source of electromagnetic energy can provide a first wavelength from a first emitter to the optical cable for a first period of time, then switch to a second emitter using an optical router to direct a second wavelength to the optical cable for a second period of time. Alternatively, the optical router could be used to provide the output of both the first and second emitters to the optical cable simultaneously. In other embodiments a source of electromagnetic energy can use a polychromatic emitter in combination with a wavelength selection device (for example, a prism or diffraction grating) that permits selection of specific wavelengths or wavelength ranges from the electromagnetic energy emitted by the polychromatic emitter, with the selected wavelength or wavelength range being directed to an optical cable.

In some embodiments of the inventive concept the source of electromagnetic energy includes a housing that encloses a processor and memory suitable for storage of data and software, which can be utilized in monitoring usage (for example, usage of emitters and optical cables), disabling the use of specific emitters and/or optical cables, and otherwise performing programmed actions that can help to ensure efficacy and safety. In other embodiment of the inventive concept the processor can be in communication with a database, and utilize data stored in the database (for example, illumination protocols). The housing can also support a mounting device that permits attachment of the source of electromagnetic energy to a suitable support, for example a IV pole or stand.

A system of the inventive concept can include a plurality of optical cables, where the optical cables interface with the source of electromagnetic energy and where specific optical cables are designated for use with specific individuals. A system or device of the inventive concept can include calibration features for performance verification, calibration, and/or adjustment of emitters and/or optical cables. Such calibration or adjustment data can also be utilized, in combination with appropriate software, to modulate transmission of light from an electromagnetic energy source to an optical cable in order to provide optimal and/or reproducible results.

In preferred aspects, a method of intravenous irradiation of blood comprises a step of using a vascular access device that includes a waveguide to transmit a first irradiation through the waveguide over a first time interval to induce a first effect within the vascular space and to transmit a second irradiation through the waveguide over a second time interval to induce a second effect within the vascular space. In a preferred embodiment of the inventive concept the second effect at least partially reverses the first effect, for example an effect produced in healthy cells or tissue of a patient irradiated by the first irradiation. Most preferably, the first irradiation comprises a UVA wavelength, a UV-B wavelength, and/or a UV-C wavelength, while the second irradiation comprises a light wavelength range of about 520 nm to about 540 nm and/or about 620 nm to about 640 nm. It should be appreciated that the first illumination, the second illumination, or both can be monochromatic or polychromatic.

It should be appreciated that methods and systems of the inventive concept provide the means for illuminating and/or irradiating vascular spaces, blood, and other body fluids, without the hazards associated with removal and return of fluid volumes and without the possibility of accidental transfer of potentially contaminated fluids between individuals. The use of multiple sources of electromagnetic energy and the ability to modulate optical communication advantageously permits the use of a single device for the implementation of complex treatment protocols (for example, simultaneous utilization of different wavelengths and/or for different time intervals). Similarly, the use of multiple patient/optical cables advantageously permits the use of a single device for the simultaneous treatment of more than one patient without the risk of cross-patient contamination. In addition, the ability to calibrate and otherwise monitor the performance of individual system components provides improved consistency, efficacy, and patient safety.

It should also be appreciated that methods and systems of the inventive concept provide the use of multiple illuminations utilizing different therapeutic wavelengths can permit the use of otherwise harmful levels of exposure by incorporating periods of illumination that reverse deleterious effects. In addition, methods of the inventive concept advantageously permit selective treatment or modification of specific cells and/or molecules within the circulatory system.

Figure 1B:
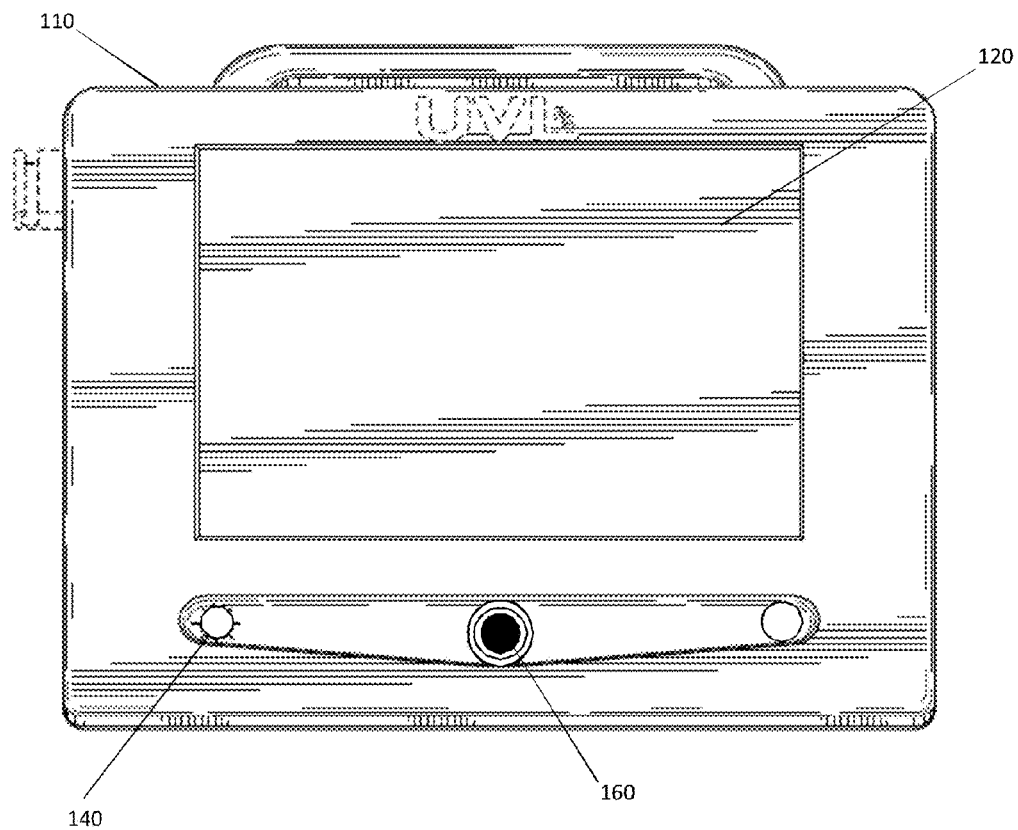

An example of an electromagnetic energy source of the inventive concept is depicted diagrammatically in FIG. 1A; a representative view of an embodiment of an electromagnetic energy source is shown in FIG. 1B. Such an electromagnetic energy source 100 can be fixed, for example, to a floor mounted device or a device that is integrated into floor mounted equipment. Alternatively, a light source of the inventive concept can be mobile, for example equipped with rollers that permit easy transit over hard or carpeted surfaces. In a preferred embodiment of the inventive concept the light source can include a mount that permits attachment of the light source to a convenient support, for example a stand of the sort utilized in the administration of intravenous fluids. Such a light source can include a housing 110, which in turn can support a mount for attachment to a stand, a display 120 (for example, as display suitable for use with a user interface), one or more optical connectors 140, and/or a calibration port 160. Such optical connectors 140 can be configured to secure optical cables 150 (patient cables) via a hub of the optical cable and to provide optical communication with one or more electromagnetic energy emitters 130. Similarly, a housing 110 of the inventive concept may enclose one or more electromagnetic energy emitters or sources 130 (EM sources). Suitable EM sources can include, but are not limited to, one or more gas laser(s), LED laser(s), and/or one or more light emitting diodes (LEDs). In a preferred embodiment of the inventive concept the EM sources include an ultraviolet emitting LED and a visible light emitting LED. In some embodiments of the inventive concept the output or intensity of such light sources can be controlled, for example by varying the energy supplied to the light source or through the use of a controllable shutter mechanism. Other embodiments of the inventive concept include a housing that encloses a circuit board, for example a circuit board that incorporates donut or annular connectors and pin (for example, pogo pin) connectors. Such a circuit board can include a processor 170, which can be configured to execute a program and/or access a database 180. Such a circuit board can also include a memory device (for example a hard drive, solid state memory, and/or RAM) that is in communication with the processor 170, and which can be configured for storage of the database 180. Alternatively, the processor 170 can be communicatively coupled to a database that exists on an external device (for example, a server) via a wired or wireless communication.

In some embodiments of the inventive concept the electromagnetic energy source can include a calibration port, which can be in optical communication with an electromagnetic energy emitter, and can be configured to interface with a calibration device. Such a calibration port can, for example, include a Luer lock-compatible fitting in such an interface. In some embodiments of the inventive concept the calibration device can provide device and/or device components specific data to a database. In still other embodiments of the inventive concept, the electromagnetic energy source can include one or more accessory ports or other interfaces that permit it to control other devices, for example an infusion pump.

Figure 2:
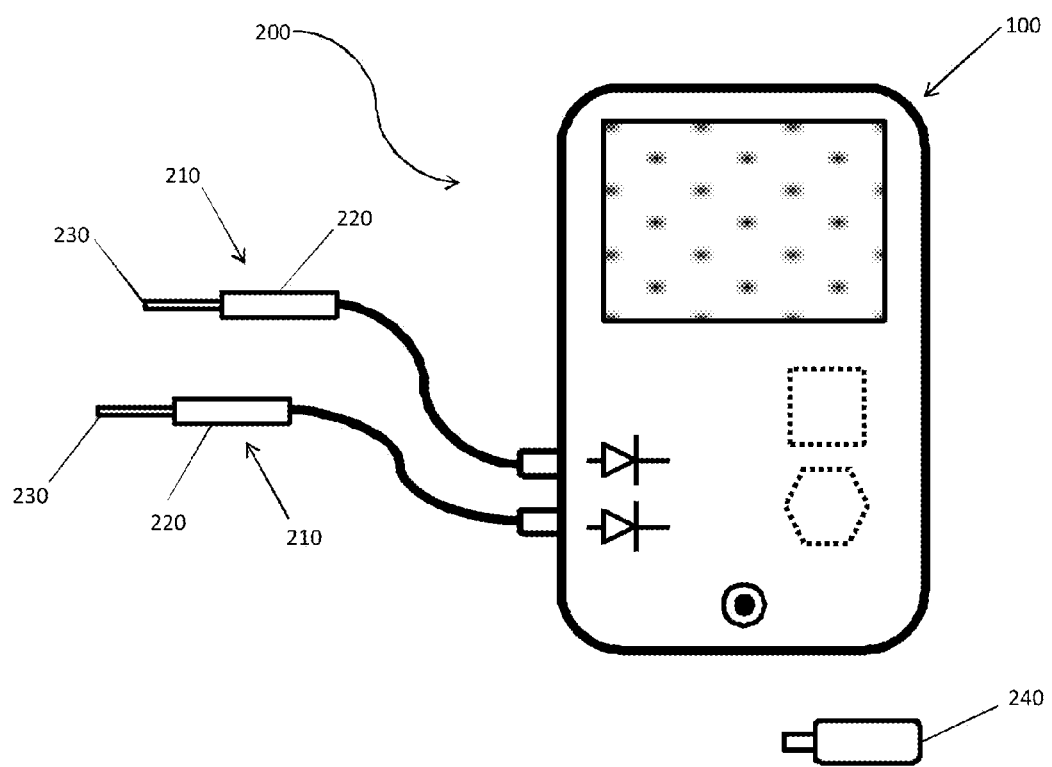
FIG. 2 provides a diagrammatic view of a system of the inventive concept.

Another embodiment of the inventive concept, as shown in FIG. 2, is a system 200 that includes an electromagnetic energy source 100 such as that described above. In some embodiments the system can include a vascular access device 210 that is configured to attach to an optical cable. Such a vascular access device 210 can include a body 220 and a waveguide 230, which, when introduced into a vascular space, can serve to introduce electromagnetic energy into a vascular space. Such a waveguide 230 can be in optical communication with an optical cable and hence to an emitter of an electromagnetic energy source 100. In some embodiments the system can include an optical calibrator 240, which can provide data useful in the characterization of light outputs from the system. For example, an optical calibrator 240 can include a photocell that produces a current when exposed to light such as that emitted by an electromagnetic energy emitter. When coupled to a calibration port of an electromagnetic energy source and in optical communication with an energized electromagnetic energy emitter, data from the optical calibrator can be used to provide data that is related to emitter intensity. Such data can, for example be used to adjust the emitter and/or identify the EM emitter as faulty. Alternatively, such data can be used to adjust an illumination protocol to provide a desired and/or consistent amount and/or intensity of electromagnetic energy to a vascular access device 210. Similarly, in some embodiments the optical calibrator 240 can be interfaced with an optical cable terminus to characterize optical cable performance. Such data can, for example, be used to identify a faulty optical cable or adjust an illumination protocol when the cable in question is utilized. In some embodiments of the inventive concept the vascular access device and/or the optical calibrator can include a Luer-compatible fitting.

As noted above, a device or system of the inventive concept can include multiple electromagnetic energy emitters or sources. Such electromagnetic energy sources can be energized and/or optically coupled (for example, using an optical switching device or router) individually, in groups, and/or collectively. In some embodiments of the inventive concept a single electromagnetic energy source can be simultaneously and/or alternatingly optically coupled to one or more optical cables. In other embodiments of the inventive concept multiple electromagnetic energy sources can be simultaneously and/or individually optically coupled to a single optical cable. This can be accomplished utilizing optical switching devices that are known in the art, and can be under the control of a processor that is executing an illumination protocol. For example, a processor can execute an illumination protocol in which a specified optical cable is optically coupled to a first electromagnetic energy source for a specified period of time and subsequently optically coupled to a second electromagnetic energy source for a second period of time. In a preferred embodiment of the inventive concept, the processor can be configured to execute one or more treatment protocols involving multiple optical cables coupled to the same electromagnetic energy source.

In some embodiments of the inventive concept, an electromagnetic energy source can provide verification of an optical connection (for example, between an optical connector and an attached optical cable. For example, a reflectance or Fresnel reflection produced by an optical interface can be characterized to determine if return loss is within acceptable limits.

Figure 3:
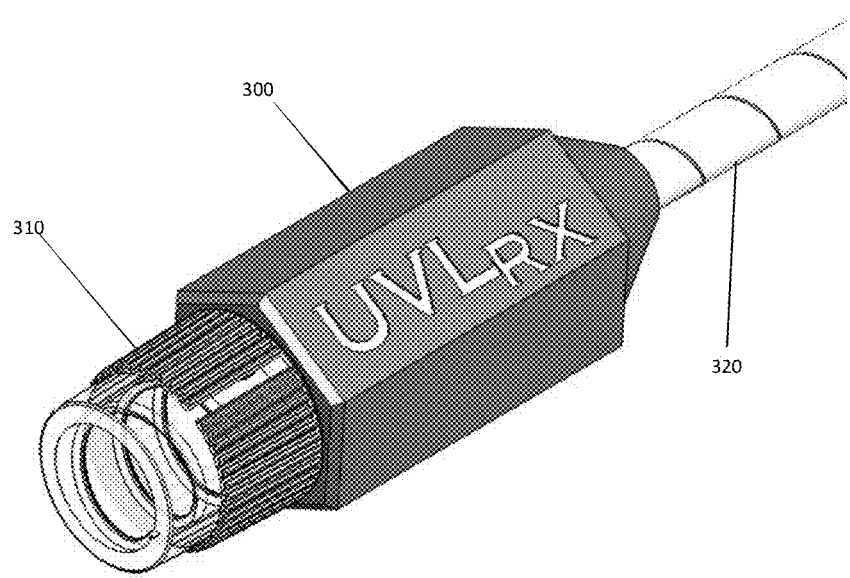
FIG. 3 shows an optical cable with a connector having an overmold.

In still other embodiments of the inventive concept the electromagnetic energy source can identify and/or track the use of a specific optical cable and/or vascular access device using any suitable indicia. For example, an optical cable can carry an RFID device that is proximal to a light source optical connector, which can in turn be equipped with an RFID antenna. Such an RFID device can, for example, be attached to or molded into an overmold 300 that is associated with a hub 310 of an optical cable 320 that provides connection to an optical connector of a light source, as shown in FIG. 3. Alternatively, an optical cable and/or vascular access device can carry a bar code that is read by a handheld scanner that is in communication with the electromagnetic energy source.

In still other embodiments of the inventive concept, an optical calibrator can be utilized to characterize the performance of an optical cable in communication with an energized electromagnetic energy source. Such an optical calibrator can, for example, include a photovoltaic device that generates an electrical potential that is related to the intensity of light to which it is exposed. Such an electrical potential can be characterized by a calibration port of the electromagnetic energy source to characterize the state of an optical cable, optical connection, and/or electromagnetic energy source. In an alternative embodiment, a calibration port can incorporate a photovoltaic device or similar mechanism for characterizing electromagnetic energy. In such an embodiment optical cable calibration can be performed using the calibration port such that the calibration port receives electromagnetic energy transmitted from an electromagnetic energy source through the optical cable. In such an embodiment both ends of an optical cable could be coupled to the electromagnetic energy source for calibration purposes.

Data related to the quality of optical connection, identity of a specific optical cable, and performance of an optical cable may be utilized to warn a user of a cable that has been used over a specified number of times or is otherwise faulty. Alternatively, data related to the quality of the optical connection and/or the identity and/or performance of a specific optical cable can be used to modify a stored illumination protocol so as to provide optimal and/or consistent results. Similarly, such information may be utilized by the processor to disallow the use of such a cable and/or re-use of a vascular access device. In some embodiments of the inventive concept data related to optical calibration, EM source duty cycles, number of optical/patient cable uses, quality of optical connection, and/or other quality or verification parameters can be stored in the database.

Figure 4:
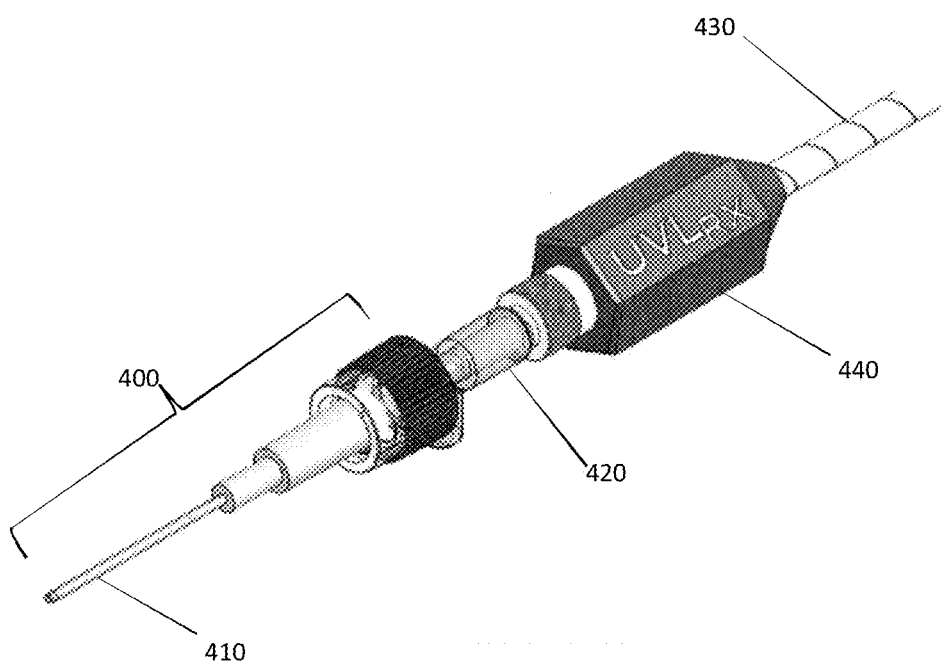
FIG. 4 shows an optical cable with an attached vascular access device.

In other embodiments of the inventive concept an optical cable can include a feature that permits identification of a specific vascular access device 400, such as is shown in FIG. 4. Such a vascular access device (VAD), for example a UVLRX® DLA™, provides for introduction of a waveguide 410 (or a portion thereof) into a vascular space of an individual, and can include a coupling feature 420 (for example, a Luer-compatible feature) that provides optical communication with an optical cable 430. In some embodiments of the inventive concept the coupling feature 420 of a VAD 400 can provide optical communication between the waveguide and an electromagnetic energy source when so coupled. In other embodiments of the inventive concept a VAD can include an identifying feature that is unique to a specific VAD, for example an RFID device. In such embodiments an optical cable can include an RFID energizer and/or RFID antenna. In a preferred embodiment of the inventive concept, such an RFID energizer and/or RFID antenna can be attached to or incorporated into an overmold 440 associated with the optical cable 430.

As described above, a device or system of the inventive concept can include a processor that can be communicatively linked to a database. Such a database can reside in local memory, such as a hard drive, solid state drive, USB drive, RAM, or other memory device and/or memory integrated into the processor itself. Alternatively, such a database may reside in an external system, such as, for example, a central server, a personal computational device (such as a smart phone, tablet computer, or wearable computer), and/or a laptop. Communication with such external systems can be through any suitable means, including wired and/or wireless connections. Such a database can receive, store, and/or transmit data related to any aspect of device or system operation. Examples of such data include, but are not limited to, illumination protocols, patient records, identity of specific consumables utilized, details of patient sessions (for example time, date, location, etc.), duty cycle of EM sources, number of times an optical cable has been connected, electromagnetic energy source and/or optical cable calibration, optical cable performance, and or quality of optical connections.

Some embodiments of the inventive concept include a user interface, which can be visualized and/or accessed via the display of the electromagnetic energy source. Such a user interface can be menu or icon driven, and can permit the creation of an illumination protocol, access a stored illumination protocol, and/or manually enter an illumination protocol for immediate use. Alternatively, all or part of the user interface may be accessed via a personal computing device, such as a smart phone, tablet computer, or wearable computer. Illumination protocols may contain information related to electromagnetic energy source or sources to be used, duration of exposure, and/or intensity of exposure. Illumination protocols can also direct the activity of external devices. For example, an illumination protocol may direct the activity of an infusion pump, thereby controlling the flow rate and type of intravenous fluids supplied to an individual during a session.

Figure 5:
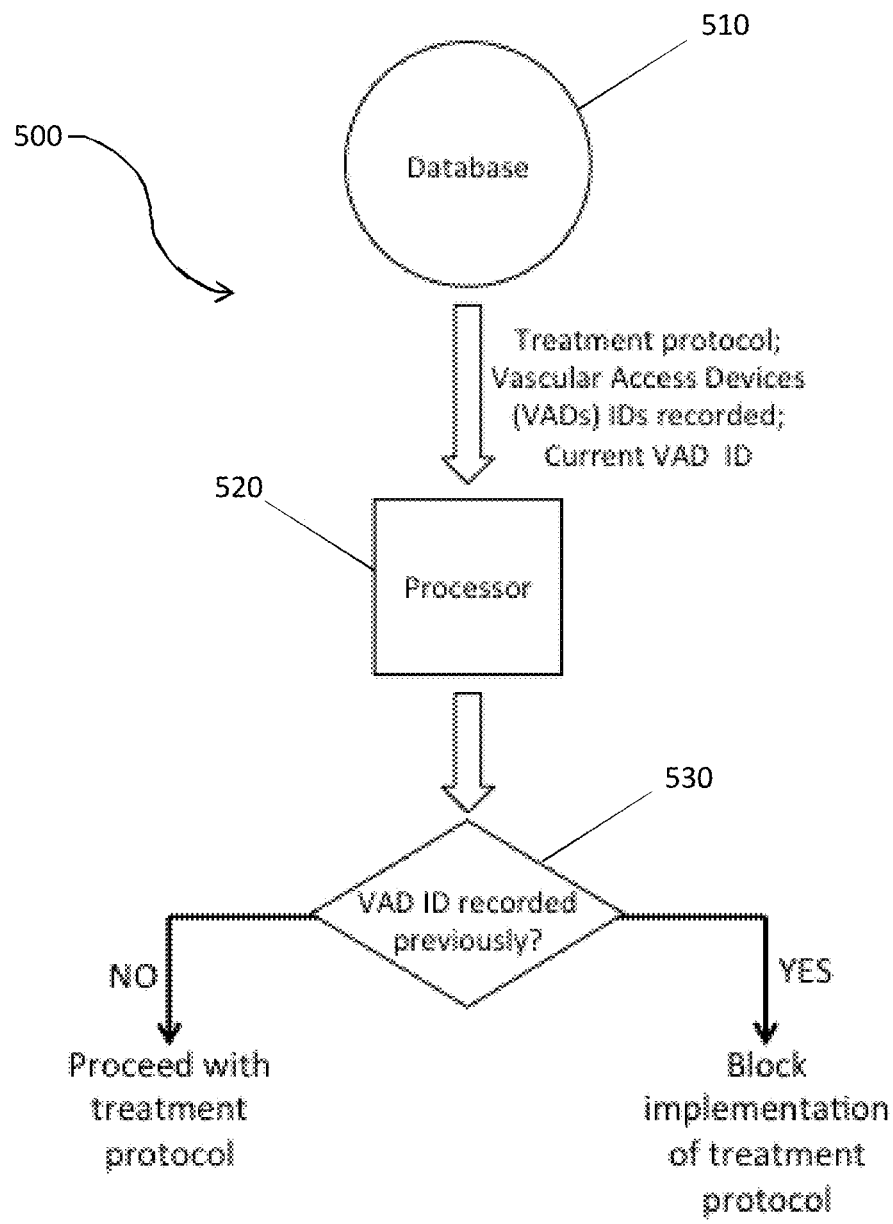
FIG. 5 is a flowchart depicting application of a rule by a system of the inventive concept.

In other embodiments of the inventive concept the processor may implement rules that override or prevent the actions specified by a user and/or by an illumination protocol, for example in response to specific calibration, verification, and or utilization data. An example of such a rule 500 is shown in the flowchart of FIG. 5. As shown, in response to a request entered via the user interface a processor 520 receives a illumination protocol to be implemented from a database 510. In addition, the processor 520 receives information that identifies the vascular access device (VAD) that has been identified as affixed to the optical/patient cable associated with the specified illumination protocol and data that includes the individual identifications of vascular access devices that have been utilized previously. The rule 500 implements a decision 530. If the vascular access device ID does not correspond to one previously used, the illumination protocol is allowed to proceed. If the vascular access device ID corresponds to one that has been used previously, implementation of the illumination protocol is blocked, thereby preventing potential contamination issues. Similarly, other rules may block implementation of a illumination protocol and/or provide user notification if, for example, a specified electromagnetic energy source or optical cable has exceeded a specified number of duty cycles, if a specified electromagnetic energy source requires excessive correction to achieve proper calibration, if an optical cable is improperly seated in an optical connector, and/or if an optical cable shows indications of damage. Use of such a rule-based hierarchal command structure advantageously helps to assure safety and optimal illumination.

In a method of the inventive concept, a vascular access device (VAD) is introduced into a vascular space, for example a vein, artery, or lymphatic channel. A VAD can include a catheter or cannula that is configured for insertion into a vascular space, a waveguide that is suitable for transmission of electromagnetic energy used for illumination, and an interface between the waveguide and an optical cable or similar source of electromagnetic energy suitable for illumination. Such a VAD can also be configured to permit administration of fluids (for example, a pharmaceutically acceptable solution) to a patient via the catheter or cannula during treatment, for example by including a fluid access port that is in fluid communication with a cannula or catheter of the VAD. Such fluids can be used to prevent the formation of clots and/or keep the VAD free of debris. In such embodiments the flow of fluid can also serve to ensure that an effective amount of electromagnetic energy reaches the vasculature, for example by removing or diluting blood (which can attenuate the electromagnetic energy being applied) within the cannula or catheter. In some embodiments such fluids can include pharmaceutical compounds, for example pharmaceutical compounds that can be activated by illumination.

In such a method, electromagnetic energy supplied by one or more electromagnetic energy sources (for example, as found in an electromagnetic energy source 100) is transmitted through an optical cable that is in optical communication with the waveguide of a VAD that has been inserted into a vascular space, such as the VAD shown in FIG. 4. Cells and molecules in the fluid that lies within the vascular space are exposed to light that exits the waveguide in this first illumination. After a period of time the electromagnetic energy transmitted through the waveguide can be changed to provide a second illumination (for example, by bringing the waveguide into optical communication with a different EM source or different set of EM sources). In some embodiments additional illumination events can be utilized as part of the therapeutic process. Such additional events can be cyclical (for example, a repetition of the first and second irradiation events) or can be a series of unique illumination events.

In such a method, illumination intensity can be selected to expose a desired volume within the vascular space. The desired volume can be selected on the basis of the wavelength or wavelength range of the illuminating electromagnetic energy, the effect desired from the illumination or both. The volume can be determined, at least in part, by considering the optical properties of blood in relation to the wavelength or wavelength range utilized for illumination. The optical properties of blood can be described by intrinsic optical parameters characteristic of the specific wavelength used: absorption coefficient $\mu_a$, scattering coefficient $\mu_s$, and anisotropy factor g. Additionally, these properties can be used to calculate the attenuation coefficient $\mu_{eff}$. For example, these parameters can be determined for diluted or physiological blood using Monte Carlo simulations, which describes the extensive extinction of ultraviolet light through whole blood (Equation I).

$$\% \ T = 1.266 \times \exp[\mu_{eff} \times z] \quad \text{Equation I}$$

Where z is the optical penetration depth and $\mu_{eff} = 107 \ mm^{-1}$. The attenuation coefficient can be calculated using Equations II and III.

$$\mu'_s = \mu_s(\lambda)(1-g(\lambda)) \quad \text{Equation II}$$

$$\mu_{eff} = \sqrt{[3\mu_a(\lambda)(\mu_a(\lambda)+\mu'_s)]} \quad \text{Equation III}$$

Figure 6:
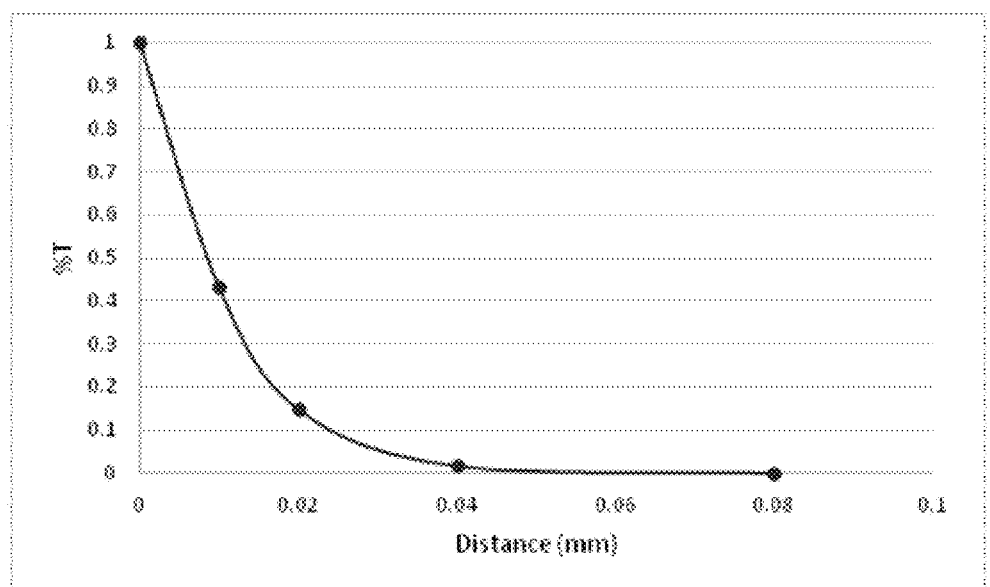
FIG. 6 depicts the calculated attenuation of ultraviolet light in whole blood.

For an ultraviolet wavelength $\lambda = 386$ nm, $\mu_a = 57.72$, $\mu_s = 64.26$, and g=0.86 at a typical physiologic hematocrit of 45%. Accordingly, % T relative to optical penetration can be calculated as shown in FIG. 6.

Light emission from a waveguide of a VAD, for example a waveguide inserted in an intravenous catheter, will propagate forward from the terminus of the waveguide (and, if the waveguide lies within a catheter) through a terminal opening of the catheter. Utilizing the attenuation calculated as shown above, the manner in which the volume of illuminated blood is calculated is dependent upon the wavelengths used. For example at a wavelength to which blood is relatively transparent (i.e. has a low optical density) the illuminated volume can be estimated using a Gaussian curve based on angular dispersion of electromagnetic energy from the terminus of the waveguide, rotated about the major axis of the illuminating waveguide at the illuminating terminus. In an embodiment of the inventive concept, the angular dispersion of electromagnetic radiation from the terminus of the waveguide ranges from 5° to 40°. In other embodiments the angular dispersion ranges from about 10° to about 30°. In a preferred embodiment the angular dispersion is about 10°. Illumination parameters (for example, wavelength, intensity, duration, frequency, etc.) can be selected to provide an amount of illuminating energy sufficient to produce a desired effect (for example, inactivation of a virus or bacteria) to a desired volume of blood as it flows through this illuminated volume.

Alternatively, at a wavelength at which blood has a high optical density, for example ultraviolet light, the volume can be estimated by calculating a cylindrical volume, where the diameter of the cylinder is essentially equivalent to the diameter of the waveguide at the emitting terminus. For example, utilizing the above equations to calculate transmittance of UVA light exiting a waveguide at 150 µW/cm$^2$ in blood shows that the effective intensity drops to essentially 0 (i.e. less than 5×10-5 µW/cm$^2$) at 0.08 mm from the illuminating terminus of the waveguide. If a waveguide with a radius of 65 µm is used, the average illumination intensity through the cylindrical volume based on this radius and an effective length of 0.08 mm gives a mean intensity of approximately 450 mW/cm$^3$ through this volume. Assuming an average blood flow of 10 cm sec$^{-1}$ provides an exposure time of a given blood volume through this cylindrical volume of approximately 2 milliseconds, yielding an effective illumination of 0.9mJ/cm$^3$. It should be appreciated that alignment of the waveguide within the blood vessel has a significant effect, and that central placement is highly desirable. Towards this end, use of a VAD that provides for a low angle of insertion into the vascular space and use of a waveguide with sufficient stiffness and resilience to maintain position within the vascular space following insertion is highly desirable.

Figure 8:
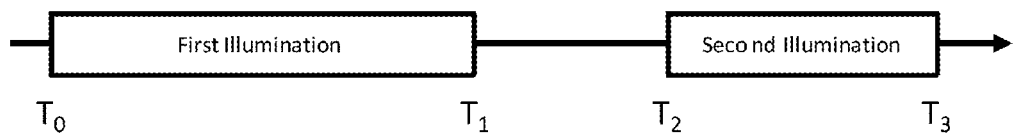
FIG. 8 schematically depicts an illumination protocol of the inventive concept.

In one embodiment of the inventive concept, such a VAD can be utilized to administer a therapeutic treatment that includes one or more periods of irradiation. An example of a timeline of such a therapeutic treatment is shown in FIG. 8. As shown, a first illumination can begin at $T_0$ and end at $T_1$, and a second illumination can begin at $T_2$ and end at $T_3$. While a rest interval from $T_1$ to $T_2$ is shown, in some embodiments of the inventive concept a second illumination can follow a first illumination with essentially no intervening rest interval. It should be appreciated that the durations of the first illumination and the second illumination can be different. Illumination can be performed for any suitably effective time interval. In some embodiments of the inventive concept the time period for a first illumination ($T_1-T_0$) can be about 1, 3, 5, 10, 20, 30, 45, 60, 90, 120, 240, 300, 360, 480, 600, or greater than 600 seconds, including at least 15 min, at least 20 min, at least 45 min, at least 60 min, etc. Similarly, the time period for the second illumination ($T_3-T_2$) can be about 1, 3, 5, 10, 20, 30, 45, 60, 90, 120, 240, 300, 360, 480, or 600, or greater than 600 seconds, including at least 15 min, at least 20 min, at least 45 min, at least 60 min, etc. The time periods of the first and second illumination can be essentially identical. In some embodiments of the inventive concept the time period of the first illumination can be greater than that of the second illumination. In other embodiments of the inventive concept the time period for the second illumination can be greater than that of the first illumination.

In some embodiments of the inventive concept, an illumination time can be selected to expose a desired volume of blood within a vascular space. The desired volume can, for example, be calculated on the basis of total blood volume (TBV). TBV varies according to a variety of parameters, including gender, height, and weight, which can in turn be used to calculate or estimate the TBV. For example, the Nadler equation (i.e. Equation III and Equation IV) has been used to estimate TBV for humans in this fashion.

Male TBV in liters=0.3669×(height in meters)$^3$× weight in kg+0.6041    Equation III Female TBV in liters=0.3561×(height in meters)$^3$× weight in kg+0.1833    Equation IV In some embodiments of the inventive concept the electromagnetic energy sources used in illumination can be selected to include wavelength ranges that produce specific effects or changes in the cells and molecules so illumination. Such effects or changes can be deleterious or otherwise impede normal function. For example, an illumination can include light ranging from 200 nm to 400 nm. Such light can result in genetic mutations and/or damage (for example the formation of thymine dimers and/or DNA strand breaks) within the DNA of exposed cells. The extent of such damage can vary between viruses and cells, and between different types of cells (for example, prokaryotic and eukaryotic cells) and different wavelengths or wavelength ranges. Selection of specific wavelengths between 200 nm and 400 nm (for example UVA, UVB, and/or UVC) can provide different effects in eukaryotic cells. For example, UVA is approximately 1000-fold less efficient in the generation of thymine dimers than UVC. Alternatively, such effects or changes can be reparative or restorative of normal function. For example, an illumination can include light ranging from 400 nm to 1200 nm and result in the activation of enzymatic and non-enzymatic reparative pathways that can repair genetic damage or reduce oxidative stress. In a preferred embodiment of the inventive concept the first illumination is configured to induce effects or changes in cells and/or molecules that are deleterious and/or impede normal function, while the second illumination is configured to at least partially reverse the effects and changes of the first illumination. In a such an embodiment of the inventive concept the reversing effects of such a second illumination can be less effective on cells and/or molecules that are deleterious (for example, bacteria, cancerous cells, and/or virus-infected cells), resulting in selective damage to such harmful cells and molecules.

It should be appreciated that in methods of the inventive concept, illumination events can be configured to have a wavelength selections, intensity, and/or duration that effects a subset of cells, viruses, and/or molecules present in a vascular space. For example, a wavelength, electromagnetic energy intensity, and duration can be selected that results in significant damage to some cells, but is relatively harmless to others. Illumination protocols can be designed with such selectivity in mind.

Similarly an illumination protocol can be configured to affect specific deleterious cells, viruses, or molecule within a vascular space. Knowledge regarding the presence of a specific pathogen in the bloodstream could permit the development or selection of a specific illumination protocols based upon that knowledge. For example, it is known that various viruses, bacteria, and eukaryotic pathogens have different degrees of susceptibility to exposure to ultraviolet light (see FIG. 7). Using such information, knowledge that *Bacillus subtilis* (reported effective UV flux=5-78 mJ/cm$^2$) was present in a bloodstream would lead to the use of an illumination protocol utilizing ultraviolet illumination at greater intensity and/or for a longer period of time than if it was known that *Vibrio cholera* was present (reported effective UV flux=0.6-4 mJ/cm$^2$). In some embodiments of the inventive concept, such information can be stored on the database 180 and accessed by a user via a user interface in order to select and/or generate an illumination protocol.

As noted in FIG. 8, different illumination events during a session may be performed for different periods of time, and in some embodiments of the inventive concept be separated by a rest interval. The intensity of a light wavelength or wavelength range can be varied between different illumination events. Similarly, in some embodiments of the inventive concept the intensity of one or more light wavelengths and/or wavelength ranges can be varied within a single illumination event.

Embodiments of the inventive concept include methods where a first illumination includes light in the wavelength range of from about 100 nm to about 280 nm (UV-C), from about 280 nm to about 315 nm (UV-B), from about 315 nm to about 400 nm (UV-A), from about 300 nm to about 500 nm, from about 200 nm to about 210 nm, from about 210 nm to about 220 nm, from about 220 nm to about 230 nm, from about 230 nm to about 240 nm, from about 240 nm to about 250 nm, from about 250 nm to about 260 nm, from about 260 nm to about 270 nm, from about 270 nm to about 280 nm, from about 280 nm to about 290 nm, from about 290 nm to about 300 nm, from about 200 nm to about 210 nm, from about 210 nm to about 220 nm, from about 220 nm to about 230 nm, from about 230 nm to about 240 nm, from about 240 nm to about 250 nm, from about 250 nm to about 260 nm, from about 260 nm to about 270 nm, from about 270 nm to about 280 nm, from about 280 nm to about 290 nm, from about 290 nm to about 300 nm, from about 300 nm to about 310 nm, from about 310 nm to about 320 nm, from about 320 nm to about 330 nm, from about 330 nm to about 340 nm, from about 340 nm to about 350 nm, from about 350 nm to about 360 nm, from about 360 nm to about 370 nm, from about 370 nm to about 380 nm, from about 380 nm to about 390 nm, from about 390 nm to about 400 nm, from about 400 nm to about 410 nm, from about 410 nm to about 420 nm, from about 420 nm to about 430 nm, from about 430 nm to about 440 nm, from about 440 nm to about 450 nm, from about 450 nm to about 460 nm, from about 460 nm to about 470 nm, from about 470 nm to about 480 nm, from about 480 nm to about 490 nm, from about 490 nm to about 500 nm, from about 500 nm to about 510 nm, from about 510 nm to about 520 nm, from about 520 nm to about 530 nm, from about 530 nm to about 540 nm, from about 540 nm to about 550 nm, from about 550 nm to about 560 nm, from about 560 nm to about 570 nm, from about 570 nm to about 580 nm, from about 580 nm to about 590 nm, from about 590 nm to about 600 nm, from about 600 nm to about 610 nm, from about 610 nm to about 620 nm, from about 620 nm to about 630 nm, from about 630 nm to about 640 nm, from about 640 nm to about 650 nm, from about 650 nm to about 660 nm, from about 660 nm to about 670 nm, from about 670 nm to about 680 nm, from about 680 nm to about 690 nm, from about 690 nm to about 700 nm, from about 700 nm to about 710 nm, from about 710 nm to about 720 nm, from about 720 nm to about 730 nm, from about 730 nm to about 740 nm, from about 740 nm to about 750 nm, from about 750 nm to about 760 nm, from about 760 nm to about 770 nm, from about 770 nm to about 780 nm, from about 780 nm to about 790 nm, from about 790 nm to about 800 nm, from about 800 nm to about 810 nm, from about 810 nm to about 820 nm, from about 820 nm to about 830 nm, from about 830 nm to about 840 nm, from about 840 nm to about 850 nm, from about 850 nm to about 860 nm, from about 860 nm to about 870 nm, from about 870 nm to about 880 nm, from about 880 nm to about 890 nm, from about 890 nm to about 900 nm, from about 900 nm to about 910 nm, from about 910 nm to about 920 nm, from about 920 nm to about 930 nm, from about 930 nm to about 940 nm, from about 940 nm to about 950 nm, from about 950 nm to about 960 nm, from about 960 nm to about 970 nm, from about 970 nm to about 980 nm, from about 980 nm to about 990 nm, from about 990 nm to about 1000 nm, and/or greater than about 1000 nm.

Other embodiments of the inventive concept include methods where a second illumination includes light in the wavelength range of from about 100 nm to about 280 nm (UV-C), from about 280 nm to about 315 nm (UV-B), from about 315 nm to about 400 nm (UV-A), from about 300 nm to about 500 nm, from about 200 nm to about 210 nm, from about 210 nm to about 220 nm, from about 220 nm to about 230 nm, from about 230 nm to about 240 nm, from about 240 nm to about 250 nm, from about 250 nm to about 260 nm, from about 260 nm to about 270 nm, from about 270 nm to about 280 nm, from about 280 nm to about 290 nm, from about 290 nm to about 300 nm, from about 200 nm to about 210 nm, from about 210 nm to about 220 nm, from about 220 nm to about 230 nm, from about 230 nm to about 240 nm, from about 240 nm to about 250 nm, from about 250 nm to about 260 nm, from about 260 nm to about 270 nm, from about 270 nm to about 280 nm, from about 280 nm to about 290 nm, from about 290 nm to about 300 nm, from about 300 nm to about 310 nm, from about 310 nm to about 320 nm, from about 320 nm to about 330 nm, from about 330 nm to about 340 nm, from about 340 nm to about 350 nm, from about 350 nm to about 360 nm, from about 360 nm to about 370 nm, from about 370 nm to about 380 nm, from about 380 nm to about 390 nm, from about 390 nm to about 400 nm, from about 400 nm to about 410 nm, from about 410 nm to about 420 nm, from about 420 nm to about 430 nm, from about 430 nm to about 440 nm, from about 440 nm to about 450 nm, from about 450 nm to about 460 nm, from about 460 nm to about 470 nm, from about 470 nm to about 480 nm, from about 480 nm to about 490 nm, from about 490 nm to about 500 nm, from about 500 nm to about 510 nm, from about 510 nm to about 520 nm, from about 520 nm to about 530 nm, from about 530 nm to about 540 nm, from about 540 nm to about 550 nm, from about 550 nm to about 560 nm, from about 560 nm to about 570 nm, from about 570 nm to about 580 nm, from about 580 nm to about 590 nm, from about 590 nm to about 600 nm, from about 600 nm to about 610 nm, from about 610 nm to about 620 nm, from about 620 nm to about 630 nm, from about 630 nm to about 640 nm, from about 640 nm to about 650 nm, from about 650 nm to about 660 nm, from about 660 nm to about 670 nm, from about 670 nm to about 680 nm, from about 680 nm to about 690 nm, from about 690 nm to about 700 nm, from about 700 nm to about 710 nm, from about 710 nm to about 720 nm, from about 720 nm to about 730 nm, from about 730 nm to about 740 nm, from about 740 nm to about 750 nm, from about 750 nm to about 760 nm, from about 760 nm to about 770 nm, from about 770 nm to about 780 nm, from about 780 nm to about 790 nm, from about 790 nm to about 800 nm, from about 800 nm to about 810 nm, from about 810 nm to about 820 nm, from about 820 nm to about 830 nm, from about 830 nm to about 840 nm, from about 840 nm to about 850 nm, from about 850 nm to about 860 nm, from about 860 nm to about 870 nm, from about 870 nm to about 880 nm, from about 880 nm to about 890 nm, from about 890 nm to about 900 nm, from about 900 nm to about 910 nm, from about 910 nm to about 920 nm, from about 920 nm to about 930 nm, from about 930 nm to about 940 nm, from about 940 nm to about 950 nm, from about 950 nm to about 960 nm, from about 960 nm to about 970 nm, from about 970 nm to about 980 nm, from about 980 nm to about 990 nm, from about 990 nm to about 1000 nm, and/or greater than about 1000 nm.

In some embodiments of the inventive concept, an illumination can be polychromatic and include electromagnetic energy from any suitable set of wavelengths and/or wavelength ranges. Such sets of wavelengths and/or wavelength ranges can be continuous or discontinuous. In one embodiment of the inventive concept a first illumination includes light with UV-A, UV-B and/or UV-C, and light in the about 620 nm to about 640 nm range (i.e red) and a second illumination includes light in the about 520 nm to about 540 nm (i.e. green) and in the about 620 nm to about 640 nm ranges. In a preferred embodiment of the inventive concept a first illumination includes light with UV-A, UV-B and/or UV-C, and a 630 nm wavelength and a second illumination includes light with 532 nm wavelength and a 630 nm wavelength.

As noted above, a source of electromagnetic energy 100 can be provided as part of a system 200 that can provide illumination to vascular access devices 210. Such a system 200 can be used to implement a method of the inventive concept. In some embodiments the system 200 can be operated manually, with a user initiating and terminating specific actions using a user interface implemented through the display 120. In a preferred embodiment, a method of the inventive concept can be implemented using an illumination protocol, by a processor 170 utilizing instructions corresponding to an illumination protocol stored on a database 180.

Illumination protocols can, for example, include instructions to direct specific wavelengths and/or wavelength ranges from electromagnetic energy emitters to a specified optical interface 140. An illumination protocol can also include instructions related to the length of time that such electromagnetic energy is directed and to the intensity of the electromagnetic energy. In some embodiments of the inventive concept, data related to the performance of an electromagnetic energy emitter, an optical interface, an optical cable, and/or a vascular access device can be used to adjust a stored baseline protocol so as to generate a nominal result. For example, should such stored data indicate that an optical cable that is in use has a small but acceptable degree of damage that reduces the light transmitted by 10%, the processor 170 could implement an optimization engine to adjust the baseline protocol stored on the database 180 to generate an optimized protocol in which the output of an electromagnetic energy source is increased to compensate for this loss. Alternatively, the optimized protocol could incorporate an increased illumination time to compensate for the transmission loss. Such adjustments can, for example, be performed based on integrating the rate at energy applied in the form of electromagnetic energy over the time that the electromagnetic energy is applied in the baseline protocol, determining an adjustment factor based upon data related to the performance of a system component to the power supplied to the electromagnetic energy emitter, the duration of the illumination period, or both, then applying the correction factor to one or both of these parameters to generate an optimized illumination protocol that is subsequently implemented. It should be appreciated that in some instances of polychromatic illumination, this can result in reducing the performance or duration of some system components (for example, a properly functioning electromagnetic energy emitter) in order to accommodate the reduce performance of a partially functioning component.

In a preferred embodiment of the inventive concept, the processor can be configured to execute one or more treatment protocols involving multiple optical cables, wherein each optical cable is utilized to provide treatment to a different individual. In some embodiments of the inventive concept such a treatment protocols can also direct the activity of external devices. For example, in some embodiments a treatment protocol can direct the activity of an infusion pump, thereby controlling the flow rate and type of intravenous fluids supplied to a patient during treatment via the VAD.

Example

An exemplary illumination session can include the following steps:

1. Turn on a suitable electromagnetic energy source, for example a UVLRX® Station, and ensure that the machine is calibrated according to manufacturer's settings.
2. Estimate the subject's total blood volume and determine treatment time. In some instances, this function can be performed by the electromagnetic energy source based upon information entered manually or accessed from a database (such as a hospital information system).
3. Put on a pair of latex-free gloves.
4. Prepare a kit that includes a vascular access device, for example a UVLRX® Patient Treatment Kit that includes a DLA™ adapter, for use by opening the kit and placing the components on a tray or table to be stationed near the patient.
5. Ready a 250 ml bag of 0.9% Sodium Chloride and an IV administration set.
6. Ready the supplied vascular access device by priming it with about 5 ml of 0.9% Sodium Chloride using a syringe. Close off the IV tubing with a slide clamp, detach the syringe, and place it aside.
7. Place a towel under the target intravenous site in order to contain any biological fluids.
8. With the patient in a relaxed semi-reclined position, identify a good IV site by visual inspection and palpation. Make sure the vein is as flat as possible to allow the intravenous catheter to lie centrally within the vein when inserted.
9. Make sure that the patient is in a comfortable position with their arm on a flat surface (for example, a pillow or arm-board. Use the patient's non-dominant arm if possible.
10. Apply the tourniquet firmly around the arm approximately 6 to 8 inches above the venipuncture site to increase pressure in vein. Leave the tourniquet in place no longer than 2 minutes.
11. Select a non-tortuous vein with a large diameter suitable for access with a 20-gauge catheter.
12. Disinfect the site of insertion with an alcohol swab, using a circular pattern and working away from the center outward to ensure proper coverage.
13. Using a 20 gauge intravenous catheter and needle assembly with the bevel oriented upward, approach the vein slowly at a low angle and perform the venipuncture with the supplied catheter and needle. Watch for blood return in the flash chamber. After flashback is observed advance the catheter until the hub is at the venipuncture site, then release the tourniquet.

14. Using moderate pressure with non-dominant thumb, occlude the vein approximately 1" above the hub. Remove the needle with dominant hand and slowly insert the waveguide extending from the DLA™ adapter into the catheter. Once fully inserted twist the spin-lock clockwise to secure it in position.

15. Secure the DLA™ to the patient's arm with tape. Tape both the site and the extending intravenous fluid tubing.

16. If gloves are soiled, discard and put on a fresh pair of latex-free gloves.

17. Reattach the syringe from step 5 to the DLA™ tubing, unlock slide clamp and push saline through the DLA™ to insure that the IV site is established.

18. Once the IV site is verified, close off the tubing with a slide clamp.

19. Remove the cap from end of IV administration kit. Remove syringe from DLA™ tubing and replace the syringe with the IV administration line.

20. Move the flow clamp on the IV administration line from the locked position to the open position and allow fluid to drip at approximately 3 ml to 4 ml per minute.

21. Prepare an optical cable for connection to the electromagnetic energy source to the vascular access device. For example, the UVLRX® Patient Cable can be prepared by removing it from the cable cradle located on left side of the UVLRX® Station. Carefully wipe the input side of the waveguide of the DLA™ (the reverse-taper portion that connects to the patient cable) with an alcohol preparation pad and ensure it is dry.

22. Attach the connector of the UVLRX® Patient Cable to the input side of the Dry Light Adaptor (DLA™), sliding it over the reverse taper portion to provide the optical connection and then turning the locking ring clockwise to secure it. Tape the IV tubing and the UVLRX® Patient Cable securely to the patient's arm.

23. Press "Start" on the UVLRX® Station to begin treatment.

24. Place all sharps and biohazards in the appropriate waste containers.

25. When the illumination session has ended disconnect the UVLRX® Patient Cable from the DLA™ by turning the locking counterclockwise to unlock, sliding the optical coupling apart, and placing the cable back into the cable cradle.

26. Place the flow clamp on the IV Administration Set to the locked position stopping the flow of saline.

27. Lock the slide clamp to ensure there is no back flow of blood.

28. Disconnect the IV Administration Set from the DLA™.

29. Using moderate pressure, occlude the vein approximately 1" above the hub and remove the DLA™ and the IV catheter together. Place a dressing on the venipuncture site.

30. Instruct the patient to hold pressure on site for several minutes.

31. Place all sharps and biohazards in the appropriate waste containers.

It should be appreciated that the above described procedure can include additional steps. For example, calibration and/or performance verification of various system components (for example, an electromagnetic energy source, an optical able, an optical interface, and/or a vascular access device) can be performed. Similarly, a vascular access device can be scanned to verify that it is appropriate for the intended use and/or has not been used previously. In other embodiments, appropriate illumination protocols can be developed, selected, or modified from base protocols to accommodate the performance characteristics of specific system components used during the session.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. An electromagnetic energy source for illumination of a vascular space, comprising;
   a plurality electromagnetic energy emitters;
   one or more optical cable connectors, wherein the optical cable connector is in optical communication with at least one of the plurality of electromagnetic energy sources;
   one or more optical cables, comprising a hub that is configured to provide an optical interface with the optical cable connectors;
   a processor, wherein the processor is configured to modulate optical communication between at least one of the plurality of electromagnetic energy emitters and the optical cable connector; and
   a database that is communicatively linked to the processor, wherein the database comprises one or more illumination protocols and stored data related to performance of a component selected from the group consisting of one of the plurality of electromagnetic energy emitters, the optical interface, the optical cable, and a vascular access device, and wherein the illumination protocol comprises instructions for modulation of an electromagnetic energy emitter, wherein the processor is configured to modify a base illumination protocol based upon the stored data to generate an adjustment factor, wherein the stored data comprises data related to the performance of the component.

2. The electromagnetic energy source of claim 1, wherein the database further comprises data consisting of a calibration of intensity of at least one of the plurality of electromagnetic energy sources.

3. The electromagnetic energy source of claim 1, further comprising a mount configured to affix the electromagnetic energy source to a pole.

4. The electromagnetic energy source of claim 1, further comprising a calibration port.

5. The electromagnetic energy source of claim 1, wherein the hub is further configured to transmit an optical cable identification to the processor.

6. The electromagnetic energy source of claim 1, wherein the plurality of optical cable connectors comprises a first optical cable connector and a second optical cable connector, wherein the plurality of electromagnetic energy emitters comprises a first electromagnetic energy emitter, and wherein the electromagnetic energy source is configured to provide optical communication between the first optical cable connector and the first electromagnetic energy emitter and between the second optical cable connector and the first electromagnetic energy emitter during the same time interval.

7. The electromagnetic energy source of claim 1, wherein the plurality of optical cable connectors comprises a first optical cable connector and wherein the plurality of electromagnetic energy emitters comprises a first electromagnetic energy emitter and a second electromagnetic energy emitter, and wherein the electromagnetic energy source is configured to provide optical communication between the first optical cable connector and the first electromagnetic energy emitter during a first time interval and to provide optical communication between the first optical cable connector and the second electromagnetic energy emitter during a second time interval.

8. The electromagnetic energy source of claim 1, wherein the plurality of optical cable connectors comprises a first optical cable connector and wherein the plurality of electromagnetic energy emitters comprises a first electromagnetic energy emitter and a second electromagnetic energy emitter, and wherein the electromagnetic energy source is configured to provide optical communication between the first optical cable connector and the first electromagnetic energy emitter and the second electromagnetic energy emitter during the same time interval.

9. The electromagnetic energy source of claim 1, further comprising an optical router.

10. A system for illumination of a vascular space, comprising;
an electromagnetic energy source comprising a plurality of electromagnetic energy emitters;
a vascular access device, comprising an optical waveguide and a catheter, wherein the optical waveguide is enclosed within the catheter of the vascular access device;
an optical cable, wherein the optical cable is in optical communication with at least one of the plurality of electromagnetic energy sources and the optical waveguide; and,
a processor; and
a database comprising one or more illumination protocols and stored data related to performance of a component selected from the group consisting of one of the plurality of electromagnetic energy emitters, the optical interface, the optical cable, and a vascular access device, and wherein the illumination protocol comprises instructions for modulation of an electromagnetic energy emitter, wherein the processor is configured to modify a base illumination protocol based upon the stored data to generate an adjustment factor, wherein the stored data comprises data related to performance of the component, wherein the processor is communicatively coupled to a database, and is configured to modulate the optical communication between at least one of the plurality of electromagnetic energy emitters and the optical cable based upon instructions stored in the database.

11. The system of claim 10, further comprising a plurality of optical cables and a plurality of vascular access devices.

12. The system of claim 10, further comprising an optical calibrator and a calibration port, wherein the calibration port is a component of the electromagnetic energy source and the optical calibrator is configured to interface with the calibration port.

13. The system of claim 12, wherein the calibration port is configured to provide optical communication between the optical calibrator and at least one of the plurality of electromagnetic energy emitters.

14. The system of claim 12, wherein the optical cable is configured to provide optical communication between the optical calibrator and at least one of the plurality of electromagnetic energy emitters.

* * * * *